United States Patent
Grey

[11] 3,938,390
[45] Feb. 17, 1976

[54] HIGH TEMPERATURE GAS SAMPLING APPARATUS AND METHOD

[76] Inventor: Jerry Grey, 359 W. 21st St., New York, N.Y. 10011

[22] Filed: Sept. 5, 1974

[21] Appl. No.: 503,916

[52] U.S. Cl. .......................................... 73/421.5 R
[51] Int. Cl.² ........................................ G01N 1/24
[58] Field of Search .... 73/190 R, 421.5 R, 421.5 A, 73/349

[56] References Cited
UNITED STATES PATENTS

| | | | |
|---|---|---|---|
| 2,682,277 | 6/1954 | Marshall et al. | 73/421.5 A |
| 3,011,336 | 12/1961 | Weiss | 73/421.5 R |
| 3,301,059 | 1/1967 | Haas | 73/190 R |
| 3,665,763 | 5/1972 | Grey | 73/190 R |

*Primary Examiner*—S. Clement Swisher
*Attorney, Agent, or Firm*—Mason, Fenwick & Lawrence

[57] ABSTRACT

A method and probe for sampling a high temperature gas mixture wherein a sample of the high temperature gas mixture withdrawn by the probe is cooled very rapidly to prevent any change in the chemical composition of the sample as it is cooled. The probe is elongated having a first passageway extending from a sampling orifice at the front end of the probe and having a rearwardly directed annular orifice in the first passageway communicating with a second passageway. The process includes the steps of inserting the front end of the probe containing the sampling orifice into the high temperature gas mixture to be sampled, extracting a gas sample through the sampling orifice, injecting a relatively cool diluent fluid under relatively high pressure through the annular orifice in the probe as the gas sample is drawn past the annular orifice and through the probe which directs the flow of the diluent fluid into the first passageway of the probe away from the sampling orifice to assist in extracting the high temperature gas mixture sample to produce a more thorough and rapid mixing of the sample of gas with the diluent fluid to preserve the chemical composition of the high temperature gas mixture. The high pressure diluent fluid expands within the first passageway to mix with the high temperature gas mixture sample thereby very rapidly cooling the sample to prevent any change in the chemical composition of the sample as it is cooled from its initial high temperature condition. The method may additionally include utilizing a probe having an external sheath containing a third and fourth passageway through which a cooling fluid is flowed to prevent the probe from melting or being damaged by the high temperature gas mixture environment.

16 Claims, 2 Drawing Figures

HIGH TEMPERATURE GAS SAMPLING APPARATUS AND METHOD

This invention relates to a method for sampling high temperature gases and more particularly to a method for sampling high temperature gas mixtures in the temperature range of 1,000° to over 30,000° F. wherein the chemical composition of a cool sample is very close to the chemical composition of the high temperature gas mixture being sampled. This invention further contemplates a novel device for sampling high temperature gas mixtures.

In aerospace and other advanced fields of technology, the temperatures at which gas samples must be taken from high temperature gas mixtures have reached levels too high for reliable operation of conventional sampling devices. The principal problem with conventional sampling devices is that as the sample of high temperature gases cools, chemical reactions take place between the constituents. Therefore, when the gas composition is finally measured at low temperature, it is very different from its original composition at high temperature. The increasing number of technologies utilizing high temperature gas mixtures and the increased demand for more precise knowledge of the chemical composition of the gas mixtures at the high temperatures experienced in these technologies has generated a demand for a method of sampling high temperature gas mixtures which is capable of producing a gas sample having a chemical composition very close to the composition of the high temperature gas mixture.

While there has been significant activity in the field of cool probes for measuring the enthalpy and the temperature of a high temperature gas mixture as described in U.S. Pat. Nos. 3,665,763 to Grey 3,296,865 to Blackshear et al. and 3,301,059 to Hass, the foregoing patents have not been capable of retaining the chemical composition of the high temperature gas mixture when it is cooled. Prior devices for sampling high temperature gas mixtures such as shown in U.S. Pat. No. 3,296,865 to Blackshear et al. have utilized a cool diluent fluid to reduce the temperature of the high temperature gas mixture to a temperature at which the gas sample can be analyzed. These prior art devices have not recognized the need to rapidly cool the high temperature gas mixture to prevent a change in the chemical composition of the sample of gas. The previous devices and systems have been concerned primarily with preventing damage to the sampling probe and the instrumentation being used to analyze the thermodynamic or physical characteristics of the gas mixture. These systems have utilized a diluent fluid flowing into the area surrounding the probe or low velocity introduction of the cooling diluent fluid into the passageway through the probe for the purpose of creating a cool outer layer surrounding the high temperature gas sample being drawn through the probe to prevent damage to the probe and to gradually cool the sample being drawn through the probe until it reaches a temperature at which the thermodynamic or physical characteristics of the sample can be measured.

Accordingly, it is the principal object of the present invention to provide a novel method and probe for sampling high temperature gas mixtures which retain the original chemical composition of the high temperature gas mixture sample when it is cooled.

Another object of the present invention is to provide a novel method and probe for sampling gas mixtures in the temperature range of 1,000° to over 30,000°F.

A further object of the present invention is to provide a novel method and probe which are capable of very rapidly cooling a high temperature gas mixture within approximately 50 microseconds.

Another object of the present invention is to provide a novel method and probe for sampling high temperature gas mixtures up to and in excess of 30,000°F. which are capable of preventing plating out of condensable gases by very rapidly cooling the gas mixture in such a fashion as to cause the condensable gases to form spheroids rather than plating out on adjacent cool surfaces.

A further object of the present invention is to provide a method and device for minimizing chemical reactions within an aspirated gas mixture during its cool down from high temperatures.

A still further object of the present invention is to provide a novel method and device for sampling high temperature gas mixtures wherein a relatively cool and diluent fluid which is combined with the aspirated high temperature gas mixture provides jet pumping to withdraw the sample from the high temperature gas mixture environment.

Another object of the present invention is to provide a novel device for sampling high temperature gas mixtures and cooling them by the addition of a relatively cool diluent fluid to the high temperature gas mixture wherein the device is capable of using a gas or liquid as the relatively cool diluent fluid.

A further object of the present invention is to provide a novel method and device for sampling high temperature gas mixtures wherein a relatively cool diluent fluid is mixed with the high temperature gas mixture samples being withdrawn through the probe and wherein the mixing occurs entirely within the probe rather than partially within the area surrounding the opening in the probe through which the high temperature gas mixture sample is withdrawn.

A still further object of the present invention is to provide a novel probe for sampling high temperature gas mixtures wherein the probe mixes a high pressure relatively cool diluent fluid into the high temperature gas mixture sample being withdrawn through the probe without having any jet flow losses caused by the injection of the cool diluent fluid.

Other objects and advantages of the present invention will become more apparent to those persons skilled in the art to which the present invention relates, from the following description taken in conjunction with the accompanying drawings, wherein.

Briefly described, the present invention relates to a novel method and probe for sampling a high temperature gas mixture wherein the probe is elongated having a first passageway extending from a sampling orifice at one end of the probe through and a second passageway communicating with an annular orifice in the first passageway. The process includes the steps of inserting the end of the probe with the sampling orifice into the gas mixture to be sampled, extracting the gas sample through the sampling orifice, and expanding a relatively cool diluent fluid such as water or helium under relatively high pressure through the annular orifice in the probe as the gas sample is drawn through the probe, thereby causing the diluent fluid to expand and mix with the high temperature gas mixture being extracted through the probe to very rapidly cool the gas mixture thereby producing a cool sample of the high temperature gas mixture retaining the chemical composition of the high temperature gas mixture. The preferred embodiment of the invention includes a means for thermally insulting the coolant flowing in the second fluid passageway from the environment of the high temperature gas mixture by providing a third fluid passageway through which a cooling fluid flows and wherein said third fluid passageway is disposed between the second fluid passageway and the environment.

Figure 1:
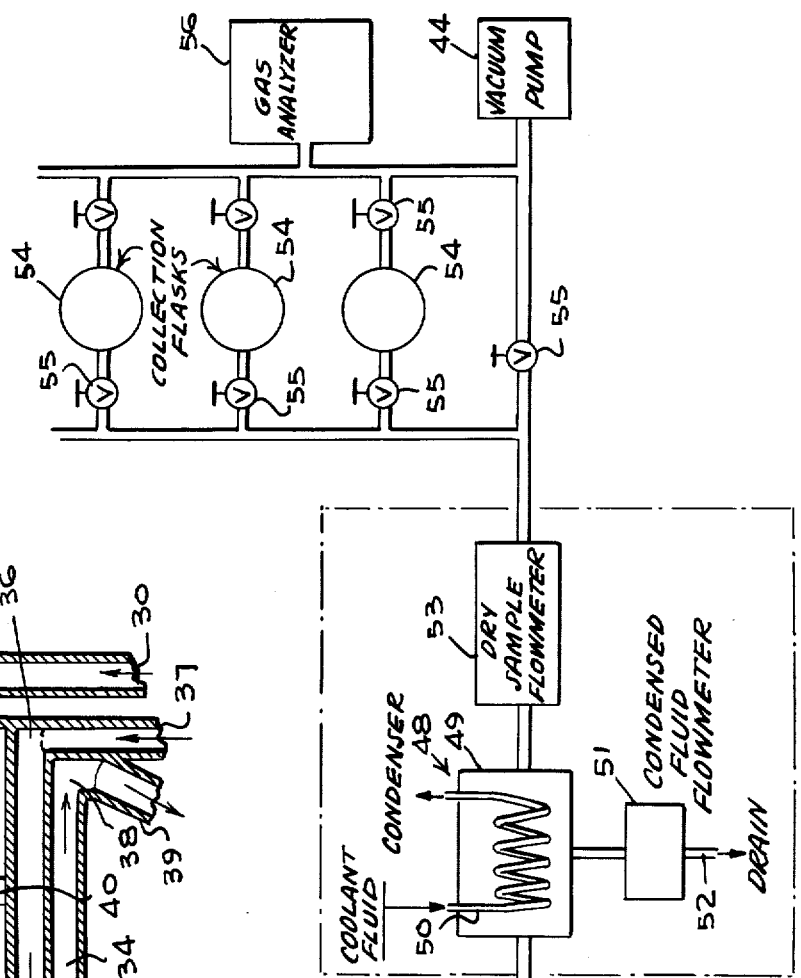
FIG. 1 illustrates an embodiment of the invention being utilized to sample a high temperature gas mixture such as the exhaust gases from a turbojet engine.

The preferred embodiment for practice of the invention includes as its primary operative member a probe body 20 having a double walled inner elongated annular jacket 21, and an outer elongated annular jacket 22 as best illustrated in FIG. 1. The inner jacket 21 includes an inner cylindrical wall 23 defining a gas sample passageway 24 having a sampling orifice 25 at the forward end thereof and an outer cylindrical wall 26 providing an annular fluid passageway 27. A forward portion 28 and the outer cylindrical wall 26 is flared inwardly and rearwardly to form a rearwardly directing deflector for fluid flowing in the direction of the arrows in the annular fluid passageway 27. The forward end 23' of the inner cylindrical wall 23 is sloped rearwardly as shown in FIG. 1 which forms in combination with the flared forward portion 28 a rearwardly directing annular orifice 29 in the gas sample passageway 24. At the end opposite the annular orifice 29, the annular fluid passageway 27 is provided with an inlet communicating with a cooling diluent fluid supply line 30.

The outer jacket 22 includes a coolant chamber inner cylindrical wall 31, an outer cylindrical wall 32, and a front end wall 33 defining a fluid passageway 34. The fluid passageway 34 is provided with a cylindrical partition wall 35 which terminates at its forward end rearwardly of the front end wall 33 to define a fluid passageway 34 wherein the inner portion of the fluid passageway 34 is provided with an inlet 36 communicating with a coolant fluid supply line 37, and the outer portion of the fluid passageway 34 is provided with an outlet 38 communicating with a coolant fluid return line 39.

It thus will be seen that fluid supplied through line 37 will flow through the inlet 36 and the inner portion of the fluid passageway 34, around the forwardly disposed end of partition wall 35 and through the outer portion of the fluid passageway 34, the outlet 38 and return line 39. Fluid introduced through the cooling diluent fluid supply line 30 will flow through the annular fluid passageway 27 and out through the rearwardly directing annular orifice 29.

The function of the gas sample passageway 24 is to receive and conduct therethrough a sample of the high temperature gas mixture being extracted from the high temperature gas mixture environment. The inner elongated annular jacket 21 is maintained in concentric relationship with the outer elongated jacket by spacers 40 which are positioned between the outer cylindrical wall 26 and coolant chamber inner cylindrical wall 31 to provide an annular insulating air gap 41 between the inner and outer jackets 31.

Figure 2:
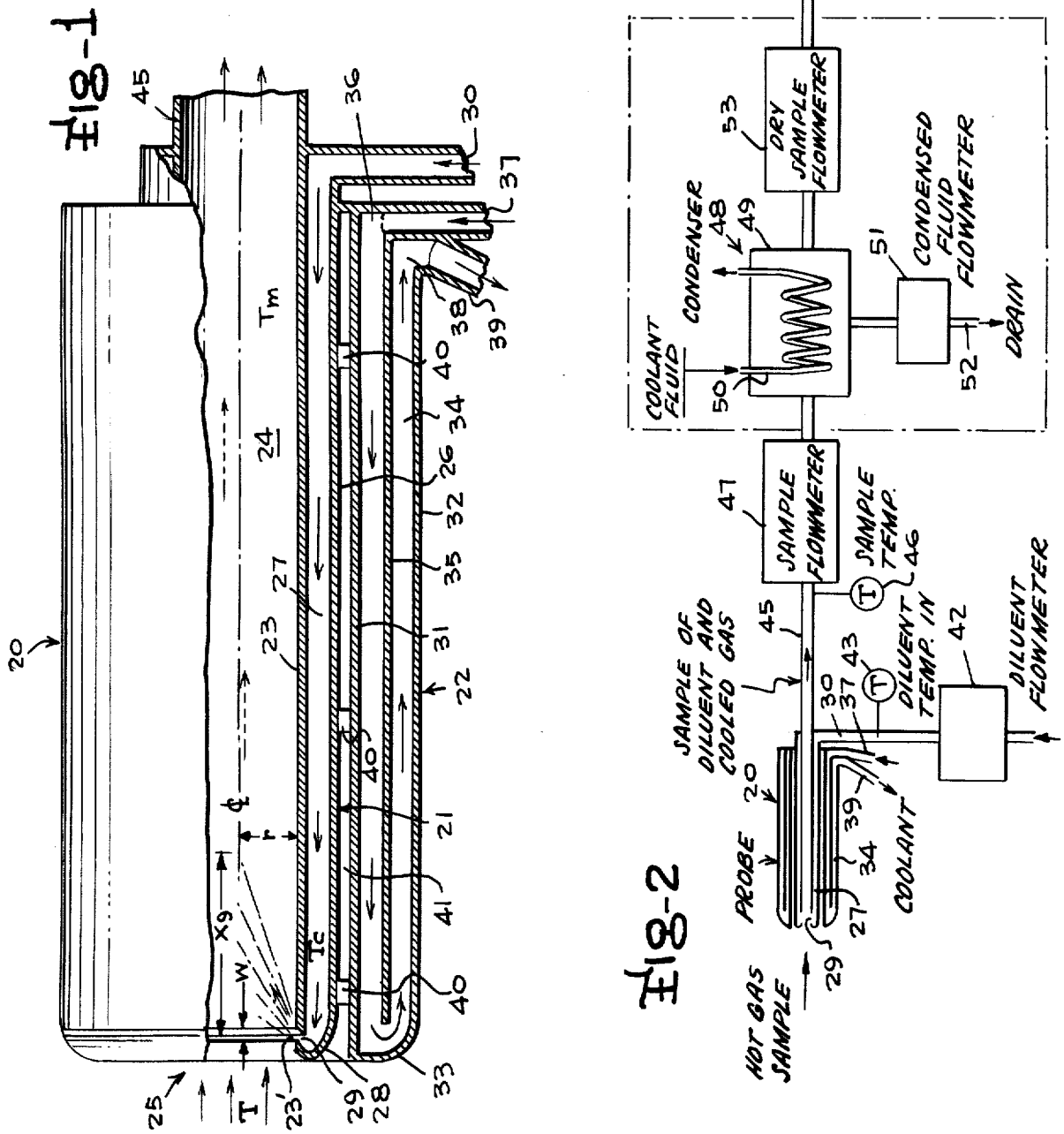
FIG. 2 is a diagramatic view of another embodiment of the invention consisting of a sampling and enthalpy or temperature measuring system utilizing a probe as illustrated in FIG. 1.

FIG. 2 illustrates a system utilizing the probe 20 of the present invention to practice the method of the present invention. The system includes the probe 20 having a coolant fluid flowing in fluid supply line 37 through the cooling fluid passageway 34 and out the fluid return line 39. A cool diluent fluid under relatively high pressure flows through the diluent fluid flowmeter 42 where the flow of diluent fluid into the probe 20 is measured and the diluent fluid then enters the supply line 30 where the temperature of the fluid is measured by a thermometer 43. The diluent fluid then flows through the annular fluid passageway 27 to be expanded as sonic or supersonic velocity through the annular orifice 29 at the forward end of the annular fluid passageway 27. A high temperature gas mixture sample is drawn through the sampling orifice 25 by the jet pumping action of the rearwardly directed discharge of diluent fluid from the annular orifice 29 and/or by operation of a vacuum pump 44. The sample of high temperature gases and diluent fluid are pushed by the jet action of the annular orifice 29 or are drawn by the vacuum pump 44 through a passageway 45 where the temperature of the cooled gas sample is measured by a sample temperature thermometer 46, through a sample flow meter 47, which measures the flow of the sample through passageway 45. The sample may then flow through the optional condensing system 48 comprising a condenser 49 having a coolant fluid flowing in cooling coil 50 to condense any condensible gases. The condensed liquid from the sample passes through a condensed fluid flowmeter 51 to the drain 52 and the dry sample passes through a dry sample flowmeter 53 into the collection flasks 54 by manipulating the various control valves 55 in an obvious manner. The samples collected in the flasks 54 may be analyzed by a gas chromatograph 56 or alternatively by a mass spectrograph, thermal conductivity cell, orsat-type analysis system or the like.

Achievement of the objects of the present invention is shown by the following analysis of the cooling time required to cool the high temperature gas mixture sample with the probe and system shown in FIGS. 1 and 2.

A high temperature gas sample as indicated in FIG. 1, at a temperature T, velocity V, density ρ flows into the sampling orifice 25 of the probe 20 under approximately isokinetic conditions; therefore, the sample velocity just inside the sampling orifice 25 is equal to the free-stream velocity. The high pressure cooling diluent fluid at a stagnation temperature $T_c$ in annular fluid passageway 27 (shown in FIG. 1) and at a stagnation pressure $P_c$ is expanded into the gas sample passageway 24 through the annular orifice 29. The gas sample, flows through the "curtain" of diluent fluid, being cooled as the sample moves through the "curtain" and mixing with the diluent fluid at the same time until it exits the "curtain" region at a temperature $T_m$. The rate of diluent fluid flow may be selected to control the final exit temperature $T_m$ within a predetermined range. This range may be selected to satisfy a desired rate of cooling, to control the condensation of constituents in the sample, or to provide sufficient cooling to prevent damage to the probe jacket.

The time necessary to reduce the temperature of the sample fluid $T$ to $T_m$ can be estimated by making several simplifying assumptions.

a. The gas properties of the sample such as mass number, specific heat at constant pressure, etc. remain at their free-stream values during mixing.
b. Characteristic mixing lengths are much smaller than the dimension of the probe which assumption is not unreasonable for the high diluent fluid velocities resulting from the high pressure diluent fluid utilized in this invention.
c. The flow is axially symmetric which assumption is consistent with the annular construction of the probe.
d. Dissipative processes may be neglected during the mixing.

If the "curtain" of diluent fluid were exactly radial (the velocity $V_c$ of the diluent fluid is infinite relative to the high temperature gas sample velocity V), assumption (b) above requires that the cooling time be simply:

$$\tau = \frac{W}{V} \qquad 1.$$

where: $\tau$ = quench time, seconds
W = annular orifice width, feet
V = velocity of gas sample, feet/second The final gas sample temperature $T_m$ is determined by the overall energy balance between the diluent fluid and the high temperature gas sample.

The actual flow pattern, however, resembles the pattern shown on FIG. 1 by dashed lines extending from the annular orifice 29, in which the ratio of the velocity of the diluent fluid to the velocity of the sample, $V_c/V$, might be on the order of one to ten, rather than being infinite. Under the assumptions (b) and (d) cooling will be complete within a time no greater than $$\tau \approx \frac{X_q}{V} = \frac{r(V/V_c)}{V} = \frac{r}{V_c} \qquad 2.$$

where $X_q$ = axial distance for full cooling, feet
r = probe inside radius, feet
$V_c$ = velocity of diluent, feet/second
and where $$V_c = \frac{m_c}{\rho_c 2\pi r W} = \frac{m_c R T'_c}{P 2 \pi r W M_c} \qquad 3.$$

where $m_c$ = the mass flow rate of the diluent fluid, pounds/second
$\rho_c$ = the density of the diluent fluid, pounds/feet$^3$
R = the universal gas constant, feet-pounds/mol°F
P = pressure of the gas sample, pounds/feet$^2$
$M_c$ = mass number of the diluent fluid, pounds/mole
or, for the usual operating condition of a sonic velocity, which is the minimum velocity, of the diluent fluid through the annular orifice 29, $$4. \quad T'_c = T_c\{2/(\gamma_c + 1)\}$$

and $$5. \quad P = P_c\{2/(\gamma_c + 1)\}^{\gamma_c/(\gamma_c-1)}$$

so that $$V_c = \frac{m_c R T_c \{(\gamma_c + 1)/2\}^{1/(\gamma_c - 1)}}{2\pi P_c r W M_c} \qquad 6.$$

where $T'_c$ = temperature of the diluent gas at the orifice, °Rankine
$T_c$ = stagnation temperature of diluent fluid, °Rankine
$\gamma_c$ = ratio of specific heats for the diluent fluid
P = pressure of the gas sample, pounds/feet$^2$
$P_c$ = stagnating pressure of diluent fluid, pounds/feet$^2$ From an energy balance, which properly does not include the heat transfer along the probe length, $$m_c = \frac{m c_p (T - T_m)}{c_{p_c}(T_m - T_c)} \qquad 7.$$

where $c_p$ = specific heat at constant pressure of the gas sample, BTU/pound - °Fahrenheit
$c_{p_c}$ = specific heat at constant pressure of the diluent fluid, BTU pounds - °Fahrenheit
and, under the conditions of assumption (a), $$m = \pi r^2 \rho V = \pi r^2 V \frac{PM}{RT} \qquad 8.$$

Thus, $$\tau = 2 \frac{2}{\gamma_c + 1}^{\frac{1}{\gamma_c - 1}} \frac{P_c}{P} \frac{M_c}{M} \frac{c_p}{c_{p_c}} \frac{T}{T_c} \frac{(T_m - T_c)}{(T - T_m)} \frac{W}{V} \qquad 9.$$

where $c_p$ = specific heat at constant pressure, BTU/pound - °Fahrenheit
M = mass number, pounds/mole
P = pressure, pounds/feet$^2$
T = temperature of the high temperature gas mixture
$T_m$ = gas/diluent mixture temperature, °Rankine
V = velocity, feet/second
W = annular orifice width, feet
$\gamma_c$ = ratio of specific heats of diluent fluid
$\tau$ = cooling time, seconds
and wherein subscripts
( )$_c$ refers to diluent fluid
(no subscript) refers to gas sample Note that the radius r of the probe gas passageway 24 does not enter into the expression explicitly. However, one of the implicit design conditions is that the annular cooling orifice width W be sufficiently narrow to ensure at least a sonic flow of the diluent fluid wherein for the diluent fluid flow rate $m_c$ needed to satisfy the overall energy balance, $2\pi r W < A^*_c$, where $A^*_c$ = critical (sonic) area, feet$^2$. Also, the total mixed gas flow after cooling cannot be allowed to choke the probe. The seemingly anomalous behaviour of the expression for cooling time, wherein $\tau$ decreases as mixed gas temperature $T_m$ decreases, results from the fact that the energy balance requires the coolant mass flow $m_c$ to increase with decreasing $T_m$, which in a constant-geometry probe causes $V_c$ to increase, reducing $\tau$.

The following example shows an application of the above relationship:
Gas sample is air,
T = 4,000R
P = 14.7 pounds/inch$^2$ = 14.7 × 144 pounds/feet$^2$
V = 100 feet/second $c_p = 0.25$
$M = 28$
Diluent/coolant is helium,
$T_c = 600°R$
$P_c = 147$ pounds/inch$^2 = 147 \times 144$ pounds/feet$^2$
$\gamma_c = 1.67$
$M_c = 4$
$W = [(.005)/12]$ feet
Required cooled gas temperature $T_m = 1,000°R$
From the derived equation 9 for cooling time:

$$\tau = 2 \left( \frac{2}{(1.67+1)} \right) \frac{1}{(1.67-1)} \frac{(10)}{1} \frac{4}{(28)} \frac{(1.25)}{(.25)} \frac{(4,000)}{(600)} \frac{(1,000-600)}{(4,000-1,000)} \frac{(.005/12)}{(100)} 10.$$

Therefore, $\tau = 22$ microseconds.

The extremely high cooling rates achievable with the present invention prevent plating out of condensable gases in passageway 24 by very rapidly cooling the gas mixture with the diluent fluid cooling "curtain" thereby causing the condensable gases to form spheroids instead of a plating out in a layer on inner cylindrical wall 23.

The outer cooled jacket 22 combined with annular insulating gap 41 isolates the inner jacket 21 from the surrounding high temperature gas mixture environment, thus making the jacket 21 a calorimeter as fully described in U.S. Pat. No. 3,665,763 to Grey. By measuring the diluent fluid mass flow rate $m_c$, its inlet temperature $T_c$, and the exit mass flow rate $m_m$ and the temperature of the cooled mixture of diluent and gas sample temperature $T_m$, the original enthalpy $h_s$ of the high temperature gas mixture can be determined as follows:

$$h_s = \frac{m_m c_{p_m} T_m - m_c c_{p_c} T_c}{m_m - m_c} \qquad 11.$$

where $c_p$ = specific heat at constant pressure of the inlet diluent fluid (known as a function of $T_c$)
$c_{p_m}$ = specific heat at constant pressure of the cooled sample (known as a function of $T_m$ and the sample composition measured by the gas analyzer 56)
$m_m$ = mass flow rate of cooled sample, lbs/sec = m + $m_c$ The probe 20 is constructed of copper, stainless steel, nickel, or other metal capable of withstanding the environment. The heat transfer requirements normally would dictate all of the designed characteristics of the probe including a passage dimension which can be as small as 0.005 inch, wall thicknesses which may be as small as 0.003 inch and the fabrication methods, as well as the overall probe configuration.

From the foregoing detailed description, it will be evident that there are a number of changes, adaptations and modiviations of the present invention which come within the province of those skilled in the at However, it is intended that all such variations not departing from the spirit of the invention be considered as within the scope thereof as limited solely by the appended claims.

I claim:

1. A process for sampling a high temperature gas mixture for minimizing chemical changes in the sample during cooling of the sample to provide a cooled sample of the mixture having a chemical composition very close to the original chemical composition of the high temperature gas mixture and for forming spheroids of the condensable constituents, said process comprising the steps of extracting a gas sample of the high temperature gas mixture, directing the sample along a passageway, expanding a relatively cool diluent fluid at or above sonic velocity and directing the expanded diluent fluid into the passageway as a conical shaped curtain of diluent fluid with the apex of the cone directed in the direction of the flow of diluent fluid and with the apex of the cone formed generally at the center of the passageway to rapidly mix the cool diluent with the high temperature gas mixture as the gas sample is extracted along the passageway.

2. A process for sampling a high temperature gas mixture according to claim 1 additionally including collecting the cool sample of gas and analyzing the collected sample to determine the chemical composition of the sample.

3. A process for sampling a high temperature gas mixture with an elongated probe having a first passageway extending from a sampling orifice at one end of the probe through the probe and a second passageway communicating with a rearwardly inclined circumferential slot in communication with said sampling orifice in the first passageway in the probe wherein a cooled sample of the high temperature gas mixture withdrawn through the probe has a chemical composition very close to the chemical composition of the high temperature gas mixture and any condensible constituents form spheroids, said process comprising inserting the end of the probe with the sampling orifice into the gas mixture to be sampled, drawing a gas sample into the probe through the sampling orifice, expanding relatively cool diluent fluid under relatively high pressure at or above sonic velocity through the rearwardly inclined circumferential slot, and directing the expanded diluent fluid into the passageway as a conical shaped curtain of diluent fluid with the apex of the cone directed in the direction of the flow of the gas sample as the gas sample is drawn through the orifice into the probe to expand the diluent fluid and mix it with the high temperature gas mixture being extracted through the probe to rapidly cool the gas mixture thereby minimizing changes in the chemical composition of the high temperature gas mixture sample and forming spheroids of any condensable constituents.

4. A process for sampling a high temperature gas mixture according to claim 3 additionally including collecting the cool sample of gas and analyzing the collected sample to determine the chemical composition of the collected sample.

5. A process for sampling a heated gas with an elongated probe having a first passageway extending along the center of the probe from a sampling orifice at one end of the probe, a second passageway concentric with the first passageway and communicating with an annular orifice in the first passageway, a third passageway concentric with the first passageway and extending over an exposed length of the probe and a fourth passageway concentric with the third passageway and communicating with the third passageway at the end of the probe adjacent the sampling orifice, wherein a cooled sample of the high temperature gas mixture retains a chemical composition very close to the chemical composition of the high temperature gas mixture, said process comprising inserting the end of the probe with the sampling orifice into the high temperature gas mixture to be sampled, extracting a gas sample through the sampling orifice, injecting relatively cool diluent fluid under relatively high pressure at or above sonic velocity through the annular orifice at an angle directed away from the sampling orifice and into the first passageway as the gas sample is drawn through the probe to expand within the first passageway, mix with the gas sample and very rapidly cool the gas sample to prevent any change in the chemical composition of the gas as it is cooled and flowing a cooling fluid through the third and fourth passageways to prevent the probe from melting or being damaged by the high temperature gas mixture.

6. A probe for sampling a high temperature gas mixture comprising a body having a sampling orifice at a forward end thereof, a first fluid passageway for receiving a gas sample therethrough from the sampling orifice, said body having a second fluid passageway for conducting a high pressure cool diluent fluid therethrough, said first passageway having a rearwardly inclined circumferential slot receiving the cool diluent fluid from the second passageway, said slot being of sufficiently narrow width to cause the high pressure cool diluent fluid to expand at or above sonic velocity through the slot and said slot directs the fluid into the first passageway and away from the sampling orifice as the sample flows through the probe.

7. A probe for sampling a high temperature gas mixture according to claim 6, wherein said first fluid passageway is elongated, and said second fluid passageway is annular and encompasses said first fluid passageway.

8. A probe for sampling a high temperature gas mixture according to claim 6, additionally including a means for thermally insulating the cooling diluent fluid flowing in the second fluid passageway from the high temperature gas mixture environment of the body.

9. A probe for sampling a high temperature gas mixture according to claim 8, wherein said means for thermally insulating includes a third fluid passageway disposed between said second fluid passageway and the environment of said body for thermally insulating the cooling diluent fluid flowing in said second fluid passageway.

10. A probe for sampling a high temperature gas mixture according to claim 9, wherein the first fluid passageway is cylindrical, the second fluid passageway is annular and encompasses said first fluid passageway, and said third fluid passageway is annular and encompasses said second fluid passageway in spaced relation.

11. A probe for sampling a high temperature gas mixture according to claim 7, additionally including a means for measuring the temperature of the cooling diluent fluid flowing into said second fluid passageway and a means for measuring the temperature of the gas sample flowing in said first fluid passageway away from the slot.

12. A probe for sampling a high temperature gas mixture according to claim 9 wherein said means for measuring the temperature of the cooling diluent fluid comprises a thermocouple disposed in the inlet of said second fluid passageway and wherein said means for measuring the temperature of the gas sample flowing in said first fluid passageway annular orifice comprises a thermocouple disposed in said first fluid passageway.

13. A probe for sampling a high temperature gas mixture according to claim 6, wherein said fluid passageways are coextensive.

14. A probe for sampling a high temperature gas mixture according to claim 6, wherein said body is metallic, said first fluid passageway is elongated, said second fluid passageway is annular and encompasses said first fluid passageway.

15. A probe for sampling a high temperature gas mixture according to claim 6, wherein said second fluid passageway is thermally insulated from said third fluid passageway.

16. A probe for sampling a high temperature gas mixture accordingly to claim 6, wherein said body is provided with a spacing between said second and third fluid passageways.

* * * * *